United States Patent
Sawada et al.

(10) Patent No.: US 8,180,018 B2
(45) Date of Patent: May 15, 2012

(54) TOMOGRAPHIC IMAGE CAPTURING APPARATUS AND TOMOGRAPHIC IMAGE CAPTURING METHOD

(75) Inventors: Hirofumi Sawada, Minami-ashigara (JP); Jun Enomoto, Kanagawa-ken (JP); Sadato Akahori, Odawara (JP); Eiichi Kanagawa, Minami-ashigara (JP); Tomoyoshi Nishimura, Tokyo (JP); Yasunori Ohta, Yokohama (JP); Noriaki Ida, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 297 days.

(21) Appl. No.: 12/654,820

(22) Filed: Jan. 5, 2010

(65) Prior Publication Data

US 2010/0172465 A1 Jul. 8, 2010

(30) Foreign Application Priority Data

Jan. 6, 2009 (JP) .................................. 2009-000960

(51) Int. Cl.
*H05G 1/60* (2006.01)
(52) U.S. Cl. ............................................. 378/11; 378/4
(58) Field of Classification Search ................ 378/4, 11, 378/19, 21–27
See application file for complete search history.

(56) References Cited

U.S. PATENT DOCUMENTS

| 6,028,910 | A | * | 2/2000 | Kirchner et al. | 378/22 |
| 7,313,219 | B2 | | 12/2007 | Endo | |
| 2008/0242968 | A1 | * | 10/2008 | Claus et al. | 600/407 |
| 2009/0041193 | A1 | * | 2/2009 | Topfer et al. | 378/108 |
| 2009/0161818 | A1 | * | 6/2009 | Sakurai et al. | 378/15 |

FOREIGN PATENT DOCUMENTS

JP 2005-137878 6/2005

* cited by examiner

*Primary Examiner* — Irakli Kiknadze
(74) *Attorney, Agent, or Firm* — Jean C. Edwards, Esq.; Edwards Neils PLLC

(57) ABSTRACT

A tomographic image capturing apparatus includes a radiation source for applying radiation to a subject at a plurality of different angles with respect to the subject, a radiation detector for detecting the radiation which has passed through the subject at each of the different angles and converting the detected radiation into image data, a tomographic image reconstructing unit for processing the image data into a reconstructed tomographic image, and an image capturing sequence setting section for establishing an image capturing sequence of a tomosynthesis image capturing process and a simple image capturing process based on ordering information which represents the tomosynthesis image capturing process for acquiring the reconstructed tomographic image and the simple image capturing process for acquiring a simple captured image.

9 Claims, 6 Drawing Sheets

TOMOGRAPHIC IMAGE CAPTURING APPARATUS AND TOMOGRAPHIC IMAGE CAPTURING METHOD

CROSS-REFERENCE TO RELATED APPLICATION

This application is based upon and claims the benefit of priority from Patent Application No. 2009-000960 filed on Jan. 6, 2009, in the Japan Patent Office, of which the contents are incorporated herein by reference.

BACKGROUND OF THE INVENTION

1. Field of the Invention

The present invention relates to a tomographic image capturing apparatus and a tomographic image capturing method for generating a tomographic image (reconstructed tomographic image) at a desired sectional position in a subject by reconstructing tomographic image data from a plurality of image data.

2. Description of the Related Art

Heretofore, tomosynthesis has been widely used for generating a tomographic image (reconstructed tomographic image) at a desired sectional position (slice height) in a subject by irradiating the subject with radiation beams emitted from a plurality of radiation sources disposed at different angles, detecting the radiation beams that have passed through the subject with a radiation detector and converting the detected radiation beams into radiographic image information (image data), and reconstructing tomographic image data from the image data.

Japanese Laid-Open Patent Publication No. 2005-137878 discloses a tomographic image capturing apparatus which is capable of performing both a tomosynthesis image capturing process for acquiring reconstructed tomographic images and a simple image capturing process for acquiring simple images.

The tomosynthesis image capturing process generates a reconstructed tomographic image by processing as many image data as several tens of images. Therefore, the tomosynthesis image capturing process requires a much longer image capturing time than the simple image capturing process which captures a single image. In other words, the tomosynthesis image capturing process poses a much larger image capturing load than the simple image capturing process because a tomographic image needs to be reconstructed from many image data. Accordingly, the tomosynthesis image capturing process consumes a long period of time to generate the reconstructed tomographic image.

If the tomographic image capturing apparatus is given ordering information that includes both the tomosynthesis image capturing process and the simple image capturing process and is controlled to capture images according to an image capturing sequence indicated by the ordering information, then it takes a long period of time until all the images are captured and the subject is released from the tomographic image capturing apparatus.

SUMMARY OF THE INVENTION

It is an object of the present invention to provide a tomographic image capturing apparatus and a tomographic image capturing method which are capable of shortening the period of time required to capture all necessary images even in the event of receiving ordering information that includes both a tomosynthesis image capturing process and a simple image capturing process.

According to the present invention, the above object can be achieved by applying radiation from a radiation source to a subject at a plurality of different angles with respect to the subject, detecting the radiation which has passed through the subject at each of the different angles and converting the detected radiation into image data, with a radiation detector, and processing the image data into a reconstructed tomographic image with a tomographic image reconstructing unit, wherein an image capturing sequence setting unit establishes an image capturing sequence of a tomosynthesis image capturing process and a simple image capturing process based on ordering information which represents the tomosynthesis image capturing process for acquiring the reconstructed tomographic image and the simple image capturing process for acquiring a simple captured image.

According to the present invention, even in the event of receiving ordering information that includes both a tomosynthesis image capturing process and a simple image capturing process, the period of time required to capture all necessary images can be shortened by establishing the image capturing sequence with the image capturing sequence setting unit.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
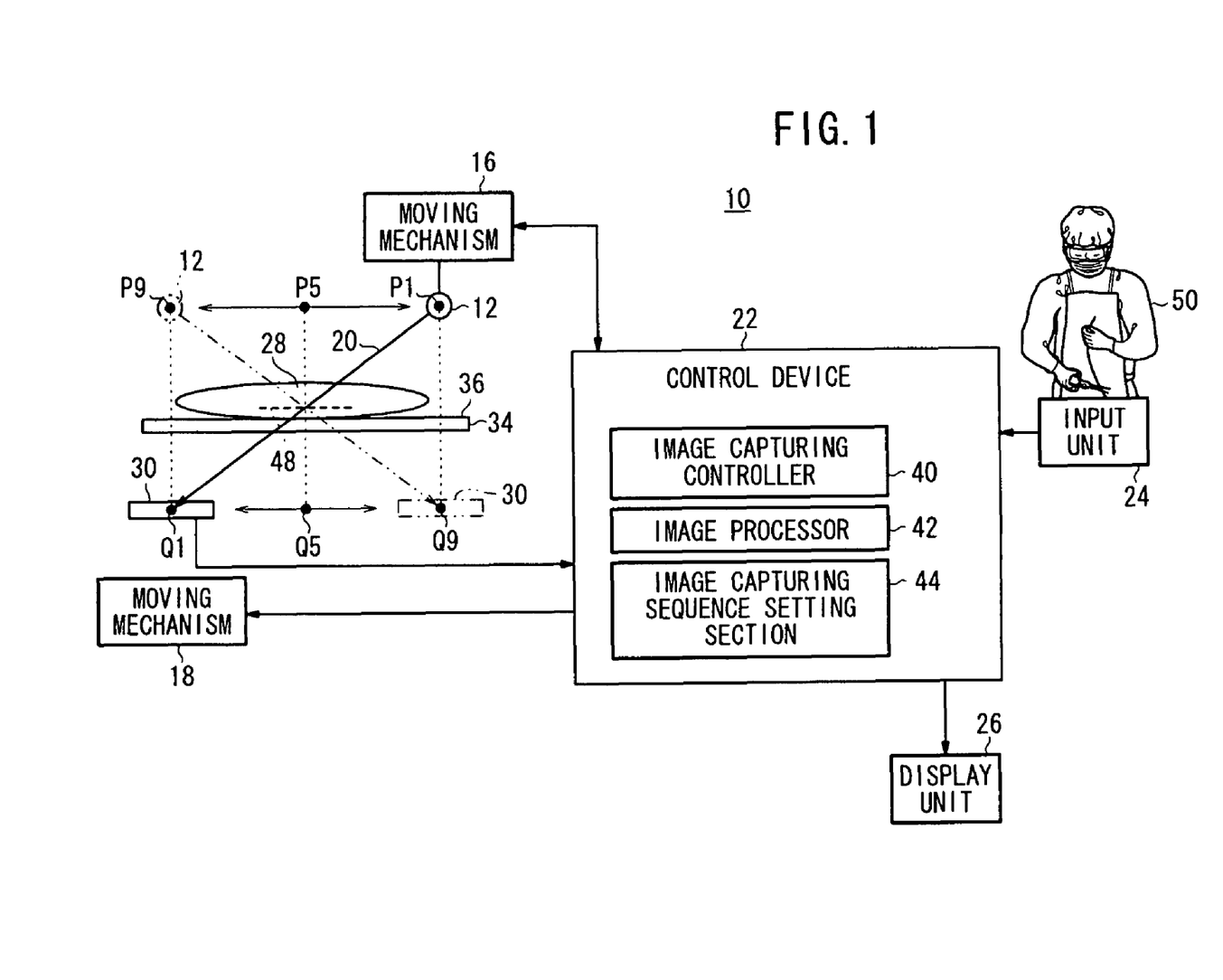
FIG. 1 is a block diagram of a tomographic image capturing apparatus according to an embodiment of the present invention.

As shown in FIG. 1, a tomographic image capturing apparatus 10 according to an embodiment of the present invention comprises a radiation source 12, a radiation conversion panel (radiation detector) 30, a first moving mechanism 16, a second moving mechanism 18, a control device 22, an input unit (input unit) 24, and a display unit (output unit) 26.

The radiation source 12 emits and applies radiation 20 at a prescribed dose to a subject 28 (e.g., a patient) lying on a lying surface 36 of an image capturing base 34 in response to a command from the control device 22. The radiation conversion panel 30 detects the radiation 20 that has passed through the subject 28, converts the detected radiation 20 into radiographic image information (image data), and outputs the radiographic image information to the control device 22. The first moving mechanism 16 moves the radiation source 12 in response to a command from the control device 22. The second moving mechanism 18 moves the radiation conversion panel 30 in response to a command from the control device 22.

The control device 22 comprises a CPU (Central Processing Unit), a memory, etc., not shown, and functionally includes an image capturing controller (control unit) 40, an image processor (tomographic image reconstructing unit) 42, and an image capturing sequence setting section (image capturing sequence setting unit) 44.

The image capturing controller 40 controls the first moving mechanism 16 to move the radiation source 12 to a desired position (angle) with respect to the subject 28, and also controls the second moving mechanism 18 to move the radiation conversion panel 30 to a desired position (angle) with respect to the subject 28.

Figure 2A:
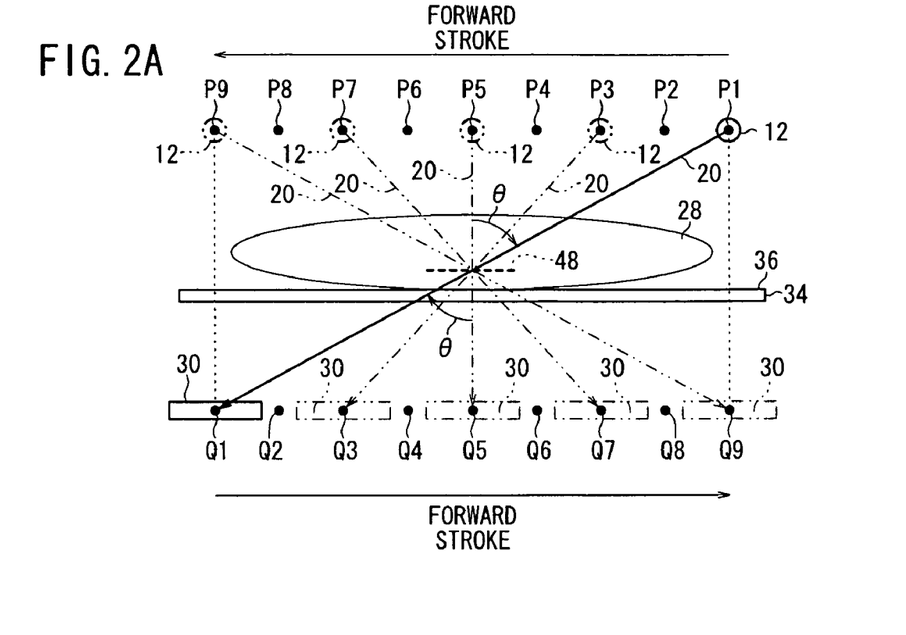
FIGS. 2A and 2B are diagrams illustrative of the manner in which a radiation source and a radiation conversion panel shown in FIG. 1 move in forward and backward strokes.
Figure 2B:
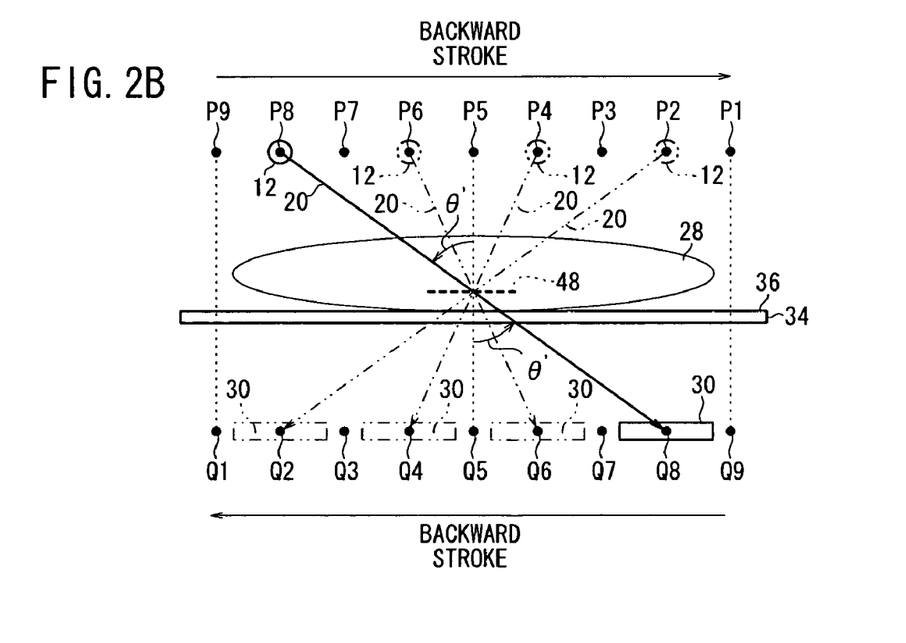

Specifically, when the tomographic image capturing apparatus 10 operates in a tomosynthesis image capturing process for acquiring a tomographic image (reconstructed tomographic image) at a sectional plane 48 at a desired sectional position (slice height) in the subject 28, the image capturing controller 40 controls the first moving mechanism 16 and the second moving mechanism 18 to move the radiation source 12 and the radiation conversion panel 30 synchronously in respective opposite horizontal directions with the subject 28 interposed therebetween while the direction in which the radiation source 12 applies the radiation 20 to the subject 28 is being held in substantial alignment with successive straight lines interconnecting positions P1 through P9 indicative of the center of the radiation source 12 and positions Q1 through Q9 indicative of the center of the radiation conversion panel 30, as shown in FIGS. 2A and 2B. While the radiation source 12 and the radiation conversion panel 30 are being moved synchronously, the image capturing controller 40 instructs the radiation source 12 to apply the radiation 20 to the subject 28 and reads the radiographic image information from the radiation conversion panel 30.

The position P1 represents a start point from which the radiation source 12 moves in a forward stroke, and also an end point to which the radiation source 12 moves in a backward stroke. The position P9 represents an end point to which the radiation source 12 moves in the forward stroke, and also a start point from which the radiation source 12 moves in the backward stroke.

The position Q1 represents a start point from which the radiation conversion panel 30 moves in a forward stroke, and also an end point to which the radiation conversion panel 30 moves in a backward stroke. The position Q9 represents an end point to which the radiation conversion panel 30 moves in the forward stroke, and also a start point from which the radiation conversion panel 30 moves in the backward stroke.

In FIG. 2A, when the radiation source 12 and the radiation conversion panel 30 move in their forward strokes, an angle θ is formed between the straight line interconnecting the points P5, Q5, which is perpendicular to the lying surface 36, and the straight lines interconnecting the positions P1 through P9 and the positions Q1 through Q9. In FIG. 2B, when the radiation source 12 and the radiation conversion panel 30 move in their backward strokes, an angle θ' is formed between the straight line interconnecting the points P5, Q5 and the straight lines interconnecting the positions P1 through P9 and the positions Q1 through Q9.

When the radiation source 12 is moved in the forward and backward directions between the positions P1 and P9 (to the positions P1 through P9) by the first moving mechanism 16, the radiation source 12 applies the radiation 20 from the positions P1 through P9 (at the angle θ or θ') to the subject 28. When the radiation conversion panel 30 is moved in the forward and backward directions between the positions Q1 and Q9 (to the positions P1 through P9) by the second moving mechanism 18, the radiation conversion panel 30 converts the radiation 20 having passed through the subject 28 into radiographic image information at the positions Q1 through Q9 (at the angle θ or θ').

The tomographic image capturing apparatus 10 captures radiographic images of the subject 28 at the positions P1 through P9, Q1 through Q9 by moving the radiation source 12 and the radiation conversion panel 30 respectively with the first moving mechanism 16 and the second moving mechanism 18, then applying the radiation 20 from the radiation source 12 to the subject 28, and thereafter converting the radiation 20 having passed through the subject 28 into radiographic image information with the radiation conversion panel 30, in a repeated manner.

As shown in FIGS. 2A and 2B, the first moving mechanism 16 may move the radiation source 12 in the forward direction from positions P1 through P3, P5 and P7 to P9, while skipping positions P2, P4, P6 and P8, and also move the radiation source 12 in the backward direction from positions P8 through positions P6 and P4 to position P2, while skipping positions P9, P7, P5, P3 and P1, and the radiation source 12 may apply the radiation 20 to the subject 28 at these unskipped positions. Accordingly, the second moving mechanism 18 may move the radiation conversion panels 30 in the forward direction from positions Q1 through positions Q3, Q5 and Q7 to position Q9, while skipping positions Q2, Q4, Q6 and Q8, and also move the radiation conversion panel 30 in the backward direction from positions Q8 through positions Q6 and Q4 to position Q2, while skipping positions Q9, Q7, Q5, Q3 and Q1, and the radiation conversion panel 30 may convert the radiation 20 having passed through the subject 28 into radiographic image information at these unskipped positions.

The radiation source 12 and the radiation conversion panel 30 may be moved to positions at desired intervals in their forward and backward strokes, rather than to the above alternate positions shown in FIGS. 2A and 2B.

As shown in FIG. 1, the image processor 42 processes radiographic image information (image data) according to a shift-and-add process or a filtered back projection (FBP) process, thereby generating a reconstructed tomographic image at the sectional plane 48, when the image capturing controller 40 reads the radiographic image information which the radiation conversion panel 30 has acquired each time the radiation source 12 applies the radiation 20 to the subject 28, i.e., each time a radiographic image of the subject 28 is captured at each position. The image processor 42 also performs various image correcting processes on the reconstructed tomographic image, including a gain adjusting process (sensitivity correcting process), an offset adjusting process (gradation correcting process), an edge enhancement process (frequency enhancement process), etc. The image processor 42 then displays the processed reconstructed tomographic image on the display unit 26, which comprises a display panel or the like.

According to the present embodiment, the tomographic image capturing apparatus 10 can also operate in a simple image capturing process for acquiring a simple image at the sectional plane 48 in the subject 28. In the simple image capturing process, the image capturing controller 40 controls the first moving mechanism 16 and the second moving mechanism 18 to move the radiation source 12 to the perpendicular position (position P5) with respect to the lying surface 36 of the image capturing base 34 and also to move the radiation conversion panel 30 to the perpendicular position (position Q5). Thereafter, the image capturing controller 40 instructs the radiation source 12 to apply the radiation 20 to the subject 28 and reads radiographic image information, which is representative of image data of a single radiographic image of the subject 28, acquired by the radiation conversion panel 30, from the radiation conversion panel 30.

In the simple image capturing process, the dose of the radiation 20 applied to the subject 28 is set to a higher level than the dose of the radiation 20 applied to the subject 28 in the tomosynthesis image capturing process.

When the image capturing controller 40 reads the above radiographic image information (image data) from the radiation conversion panel 30, the image processor 42 can perform the same image correcting processes as described above on the radiographic image information and thereafter display the corrected simple captured image on the display unit 26.

The input unit 24 serves to input commands as ordering information from a doctor (or radiographic technician) 50 for the tomosynthesis image capturing processes and the simple image capturing processes. The input unit 24 may comprise operating buttons, a keyboard, a mouse, etc., for example.

When the image capturing sequence setting section 44 is supplied with ordering information that includes a tomosynthesis image capturing process and a simple image capturing process, from the input unit 24, the image capturing sequence setting section 44 establishes an image capturing sequence for the tomosynthesis image capturing process and the simple image capturing process, and outputs image capturing sequence setting information representative of the established image capturing sequence to the image capturing controller 40. The image capturing controller 40 then performs the tomosynthesis image capturing process and the simple image capturing process according to the image capturing sequence represented by the image capturing sequence setting information.

Specifically, if (1) the supplied ordering information includes a tomosynthesis image capturing process and a simple image capturing process, then the image capturing sequence setting section 44 generates image capturing sequence setting information representative of an image capturing sequence for the tomosynthesis image capturing process and the simple image capturing process such that the simple image capturing process will be performed prior to the tomosynthesis image capturing process or while the image processor 42 is generating a reconstructed tomographic image in the tomosynthesis image capturing process. If (2) the supplied ordering information includes a plurality of tomosynthesis image capturing processes and a simple image capturing process, then the image capturing sequence setting section 44 generates image capturing sequence setting information representative of an image capturing sequence for the tomosynthesis image capturing processes and the simple image capturing process such that the simple image capturing process will be performed prior to each of the tomosynthesis image capturing processes or between the tomosynthesis image capturing processes or while the image processor 42 is generating a reconstructed tomographic image in either one of the tomosynthesis image capturing processes.

If the image capturing sequence setting section 44 is supplied with new ordering information which includes a simple image capturing process while the tomographic image capturing apparatus 10 is capturing images of the subject 28 (in the tomosynthesis image capturing process and the simple image capturing process) based on the generated image capturing sequence setting information, then the image capturing sequence setting section 44 generates new image capturing sequence setting information representative of a re-established image capturing sequence for performing the simple image capturing process either while a reconstructed tomographic image is being generated in each of the tomosynthesis image capturing processes or between the tomosynthesis image capturing processes, and outputs the generated new image capturing sequence setting information to the image capturing controller 40. When the image capturing controller 40 is supplied with the new image capturing sequence setting information, the image capturing controller 40 performs the tomosynthesis image capturing processes and the simple image capturing process according to the re-established image capturing sequence represented by the new image capturing sequence setting information.

Basic details of the tomosynthesis image capturing processes and the simple image capturing process are disclosed in Japanese Laid-Open Patent Publication No. 2005-137878, and will not be described in detail below.

The tomographic image capturing apparatus 10 according to the present embodiment is configured as described above.

Operation (tomographic image capturing method) of the tomographic image capturing apparatus 10 will be described below with reference to flowcharts shown in FIGS. 3 through 6.

Figure 3:
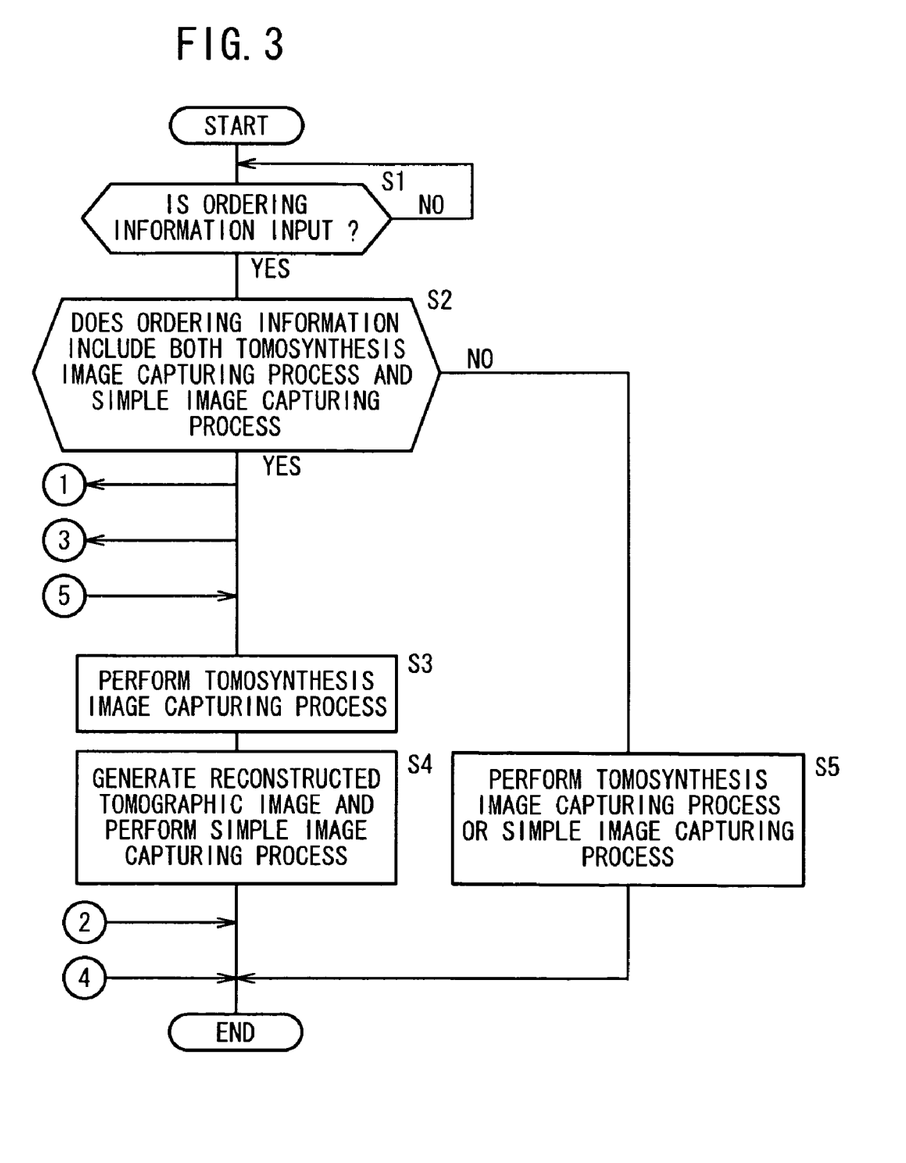
FIG. 3 is a flowchart of an operation sequence of the tomographic image capturing apparatus shown in FIG. 1 for carrying out a tomosynthesis image capturing process and a simple image capturing process.

FIG. 3 is a flowchart of an operation sequence of the tomographic image capturing apparatus 10 at the time the control device 22 (see FIG. 1) is supplied with ordering information for carrying out one tomosynthesis image capturing process and one simple image capturing process.

In step S1 shown in FIG. 3, the control device 22 determines whether ordering information has been input to the input unit 24 by the doctor 50 or not. If no ordering information has been input to the input unit 24 ("NO" in step S1), then the control device 22 continues to perform step S1. If ordering information has been input to the input unit 24 ("YES" in step S1), then the image capturing sequence setting section 44 of the control device 22 determines whether the ordering information includes both a tomosynthesis image capturing process and a simple image capturing process or not, in step S2.

If the ordering information includes both a tomosynthesis image capturing process and a simple image capturing process ("YES" in step S2), then the image capturing sequence setting section 44 generates image capturing sequence setting information representative of an image capturing sequence for performing the simple image capturing process while a reconstructed tomographic image is being generated in the tomosynthesis image capturing process, and outputs the generated image capturing sequence setting information to the image capturing controller 40.

The image capturing controller 40 then performs the tomosynthesis image capturing process and the simple image capturing process according to the image capturing sequence represented by the image capturing sequence setting information in steps S3, S4.

Specifically, in step S3, the tomosynthesis image capturing process is carried out as follows: The image capturing controller 40 controls the first moving mechanism 16 and the second moving mechanism 18 to move the radiation source 12 and the radiation conversion panel 30 synchronously in respective opposite horizontal directions with the subject 28 interposed therebetween, and at the same time controls the radiation source 12 to apply the radiation 20 to the subject 28 and also controls the radiation conversion panel 30 to detect the radiation 20 that has passed through the subject 28 and convert the radiation 20 into radiographic image information (image data).

When all radiographic image information necessary in the tomosynthesis image capturing process is acquired, the image processor 42 of the control device 22 processes all the image data into a reconstructed tomosynthesis image, and displays the reconstructed tomosynthesis image on the display unit 26, in step S4.

While the reconstructed tomosynthesis image is being generated by the image processor 42, the image capturing controller 40 controls the first moving mechanism 16 and the second moving mechanism 18 to move the radiation source 12 to the position P5 (see FIGS. 2A and 2B) and also move the radiation conversion panel 30 to the position Q5. Thereafter, the image capturing controller 40 controls the radiation source 12 to apply the radiation 20 to the subject 28 and reads radiographic image information (image data) from the radiation conversion panel 30. The image processor 42 performs given image correcting processes on the image data read from the radiation conversion panel 30 by the image capturing controller 40, and displays the corrected image data (simple captured image) on the display unit 26.

In step S4, therefore, the image processor 42 can display both the reconstructed tomosynthesis image and the simple captured image on the display unit 26.

In the above simple image capturing process, the dose of the radiation 20 applied to the subject 28 is set to a higher level than the dose of the radiation 20 applied to the subject 28 in the tomosynthesis image capturing process.

If the ordering information includes either a tomosynthesis image capturing process or a simple image capturing process ("NO" in step S2), then the control device 22 performs the tomosynthesis image capturing process or the simple image capturing process in the same manner as with step S3 or S4 in step S5.

In the present embodiment, one simple image capturing process is performed while the reconstructed tomosynthesis image is being generated in one tomosynthesis image capturing process. However, an operation sequence represented by a flowchart shown in FIG. 4 may be carried out instead of steps S3, S4 shown in FIG. 3.

Figure 4:
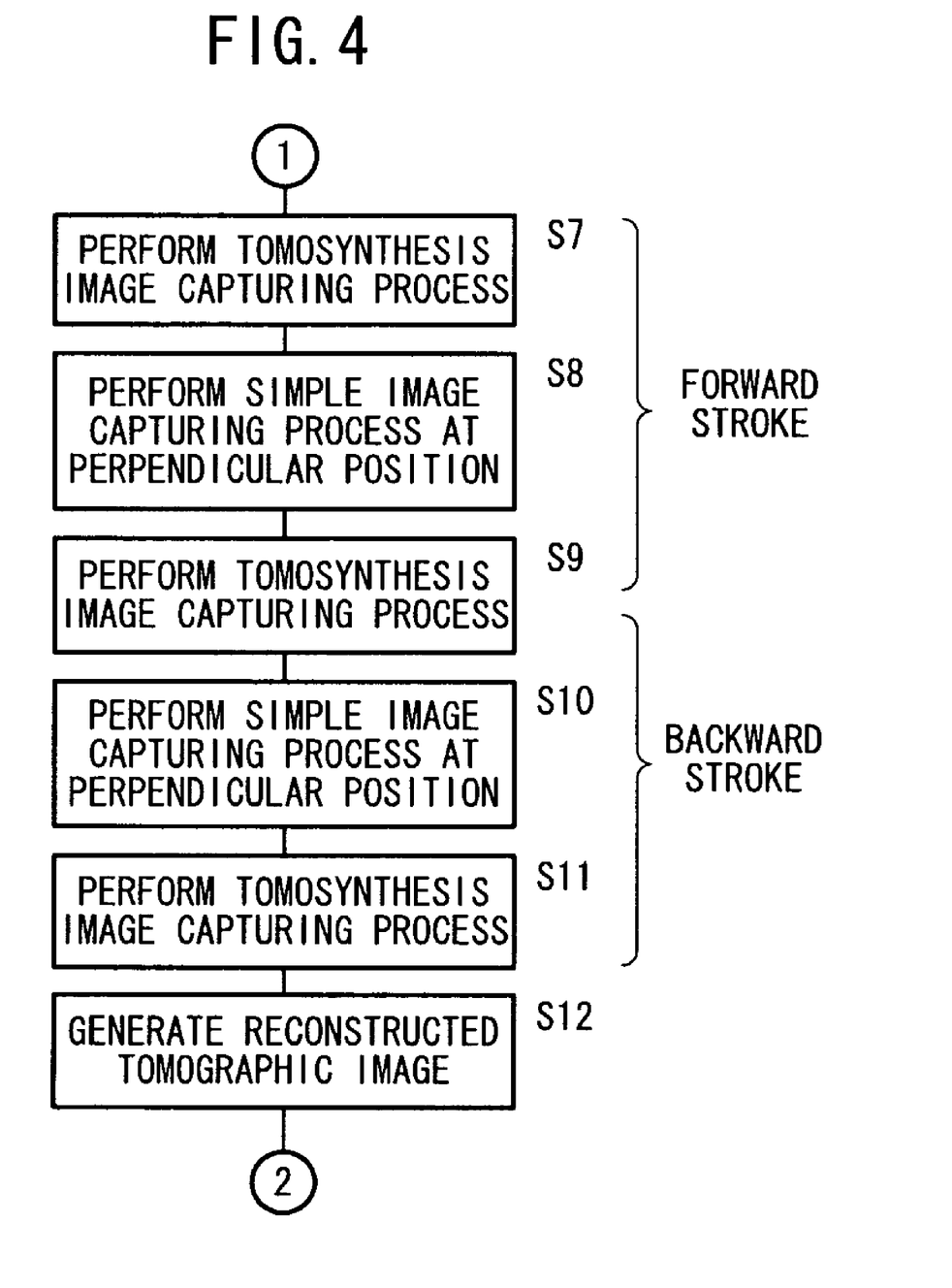
FIG. 4 is a flowchart of another operation sequence for carrying out a tomosynthesis image capturing process and a simple image capturing process.

FIG. 4 is a flowchart of an operation sequence for carrying out simple image capturing processes in one tomosynthesis image capturing process. According to the operation sequence shown in FIG. 4, the simple image capturing processes are carried out as part of the tomosynthesis image capturing process.

In step S7 shown in FIG. 4, the image capturing controller 40 controls, as in the above-described step S3, the first moving mechanism 16 and the second moving mechanism 18 to move the radiation source 12 from the position P1 to the position P5 (see FIG. 2A) in the forward stroke and also to move the radiation conversion panel 30 from the position Q1 to the position Q5 in the forward stroke, while performing the tomosynthesis image capturing process.

When the radiation source 12 is moved to the position P5 and the radiation conversion panel 30 to the position Q5, the dose of the radiation 20 applied to the subject 28 is set to a higher level than the dose of the radiation 20 applied to the subject 28 at the positions P1 through P4, and the image capturing controller 40 performs a simple image capturing process in step S8.

In step S9, the image capturing controller 40 moves the radiation source 12 from the position P5 to the position P9 in the forward stroke and also moves the radiation conversion panel 30 from the position Q5 to the position Q9 in the forward stroke, while performing the tomosynthesis image capturing process, as with steps S3, S7. In step S9, the dose of the radiation 20 applied to the subject 28 is set to a lower level than the dose of the radiation 20 applied to the subject 28 in the simple image capturing process of step S8, i.e., is returned to the dose of the radiation 20 applied to the subject 28 in step S7.

When the radiation source 12 is moved to the position P9 and the radiation conversion panel 30 to the position Q9 in step S9, the image capturing controller 40 controls the first moving mechanism 16 and the second moving mechanism 18 to move the radiation source 12 from the position P9 to the position P5 (see FIG. 2B) in the backward stroke and also to move the radiation conversion panel 30 from the position Q9 to the position Q5 in the backward stroke, while performing the tomosynthesis image capturing process.

When the radiation source 12 is moved to the position P5 and the radiation conversion panel 30 to the position Q5, the image capturing controller 40 performs a simple image capturing process again, in step S10 in the same manner as with step S8.

In step S11, the image capturing controller 40 returns (reduces) the dose of the radiation 20 to the dose in steps S7, S9, and moves the radiation source 12 from the position P5 to the position P1 in the backward stroke and moves the radiation conversion panel 30 from the position Q5 to the position Q1 in the backward stroke, while performing the tomosynthesis image capturing process.

When the image capturing processes in the forward stroke and the backward stroke are finished and all the necessary radiographic image information is captured, the image processor 42 processes all the image data into a reconstructed tomosynthesis image, and displays the reconstructed tomosynthesis image and the simple captured images on the display unit 26 in step S12.

Figure 5:
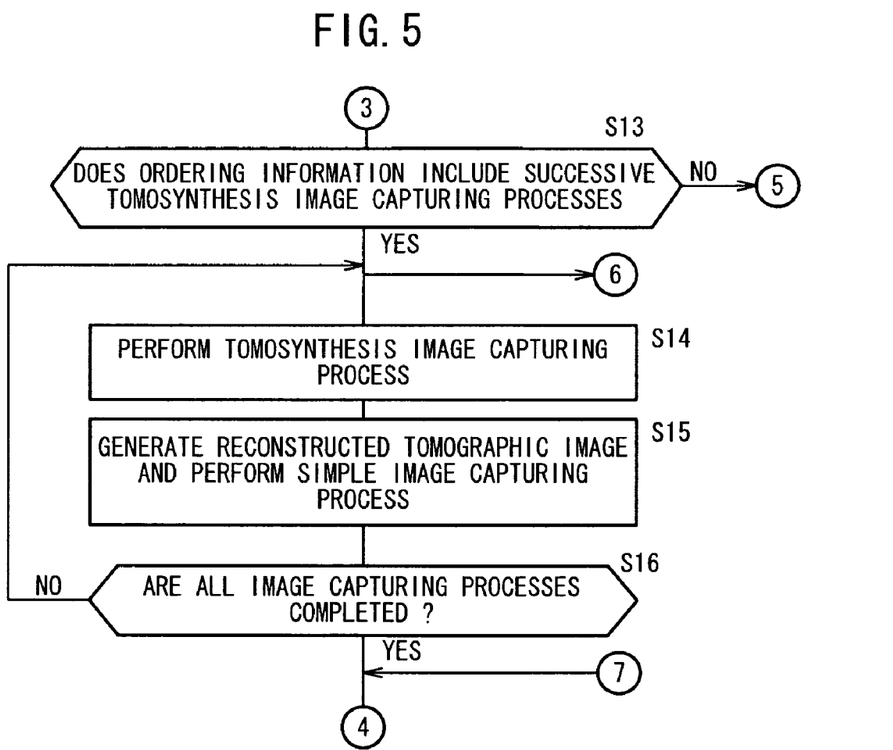
FIG. 5 is a flowchart of still another operation sequence for carrying out a tomosynthesis image capturing process and a simple image capturing process.

Steps S3, S4 shown in FIG. 3 or the operation sequence shown in FIG. 4 may be replaced with an operation sequence shown in FIG. 5.

FIG. 5 shows an operation sequence in a case where ordering information for carrying out a plurality of tomosynthesis image capturing processes and one or more simple image capturing processes is input.

In step S13 shown in FIG. 5, the image capturing sequence setting section 44 determines whether the ordering information includes a plurality of successive tomosynthesis image capturing processes or not. If the ordering information includes a plurality of successive tomosynthesis image capturing processes ("YES" in step S13), then the image capturing sequence setting section 44 generates image capturing sequence setting information representative of an image capturing sequence for performing a simple image capturing process while a reconstructed tomographic image is being generated in each of the tomosynthesis image capturing processes, and outputs the generated image capturing sequence setting information to the image capturing controller 40.

The image capturing controller 40 performs the tomosynthesis image capturing processes according to the image capturing sequence represented by the image capturing sequence setting information in step S14, and performs simple image capturing processes while reconstructed tomographic images are being generated by the image processor 42 in step S15. In step S16, the image capturing controller 40 determines whether all image capturing processes indicated by the image capturing sequence setting information are completed or not. If there are any tomosynthesis image capturing processes and simple image capturing processes to be carried out ("NO" in step S16), then control goes back to step S14, and steps S14, S15 are performed again. If all image capturing processes indicated by the image capturing sequence setting information are completed ("YES" in step S16), then the operation of the tomographic image capturing apparatus 10 is ended.

If the ordering information includes one tomosynthesis image capturing processes and one simple image capturing process ("NO" in step S13), then the control device 22 carries out steps S3, S4 shown in FIG. 3.

Figure 6:
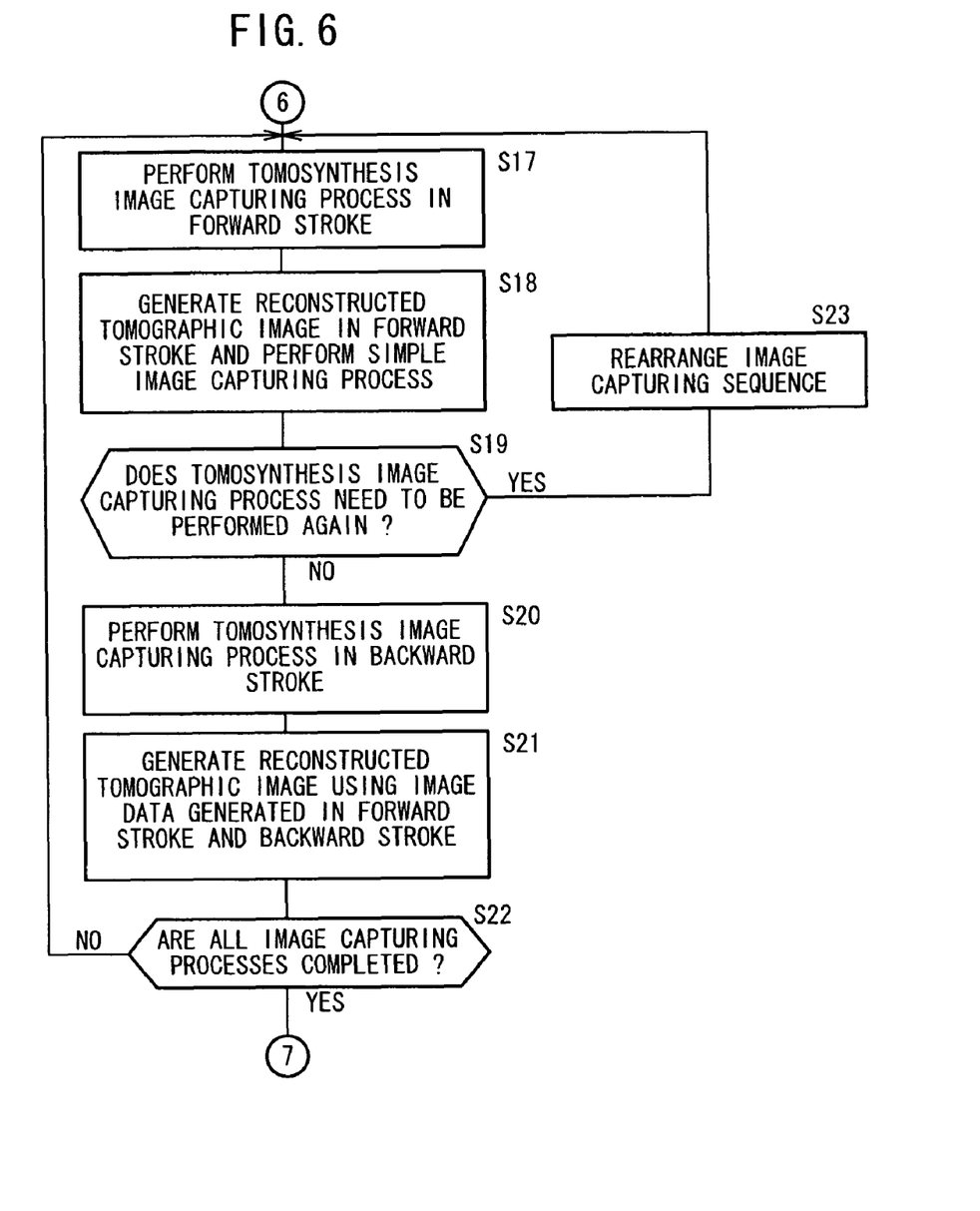
FIG. 6 is a flowchart of yet another operation sequence for carrying out a tomosynthesis image capturing process and a simple image capturing process.

Steps S14 through S16 shown in FIG. 5 may be replaced with an operation sequence shown in FIG. 6.

The operation sequence shown in FIG. 6 serves to generate a reconstructed tomographic image again quickly in the event that the reconstructed tomographic image which has been generated is inappropriate because it contains an image blur due to an unwanted movement of the subject 28 being imaged or the dose of the radiation 20 applied to obtain the reconstructed tomographic image which has been generated falls out of a desired dose range. The image blur refers to an adverse image condition caused when the subject 28 moves a certain distance or greater between a plurality of compared image data which are processed into the reconstructed tomographic image.

In step S17 shown in FIG. 6, a tomosynthesis image capturing process is performed in a forward stroke and all necessary radiographic image information (image data) is acquired. Then, in step S18, the image processor 42 processes the image data into a reconstructed tomographic image in the forward stroke, and the image capturing controller 40 carries out a simple image capturing process in the same manner as with step S4 shown in FIG. 3.

In step S19, the image capturing controller 40 determines whether a tomosynthesis image capturing process is to be performed in a backward stroke or not based on the reconstructed tomographic image.

If the image capturing controller 40 judges that the reconstructed tomographic image is adequate for diagnosis ("NO" in step S19), then it decides to perform a tomosynthesis image capturing process in a backward stroke. The image capturing sequence setting section 44 displays the reconstructed tomographic image in the forward stroke and the decision to perform the tomosynthesis image capturing process in the backward stroke on the display unit 26. Based on the decision, the image capturing controller 40 controls the first moving mechanism 16 and the second moving mechanism 18 to perform the tomosynthesis image capturing process in the backward stroke in step S20.

When the tomosynthesis image capturing process in the backward stroke is finished and all necessary radiographic image information (image data) is acquired, the image processor 42 processes all the image data in the forward stroke and the backward stroke into a new reconstructed tomographic image in step S21. The display unit 26 displays the new reconstructed tomographic image generated by the image processor 42 and the simple captured image acquired in step S18.

If all the image capturing processes indicated by the image capturing sequence setting information are completed ("YES" in step S22), the operation of the tomographic image capturing apparatus 10 is ended.

If the image capturing controller 40 judges that the reconstructed tomographic image is inadequate for diagnosis ("YES" in step S19), then the image capturing sequence setting section 44 re-establishes (rearranges) an image capturing sequence and generates new image capturing sequence setting information in step S23. Control then goes back to step S17 to perform tomosynthesis and simple image capturing processes based on the new image capturing sequence setting information.

If there are any tomosynthesis image capturing processes and simple image capturing processes to be carried out ("NO" in step S22), then control goes back to step S17, and steps S17 through S21 are performed again.

With the tomographic image capturing apparatus 10 and the tomographic image capturing method according to the present embodiment, even if the ordering information includes both a tomosynthesis image capturing process and a simple image capturing process, the image capturing sequence setting section 44 establishes an image capturing sequence to shorten the period of time required to perform all the image capturing processes.

Specifically, the image capturing sequence setting section 44 establishes an image capturing sequence for performing a simple image capturing process prior to a tomosynthesis image capturing process which requires a long period of time to generate a reconstructed tomographic image or while a reconstructed tomographic image is being generated. Therefore, a simple captured image in the simple image capturing process can quickly be acquired, and the entire period of time required to perform all the image capturing processes can be shortened. According to the present embodiment, therefore, the period of time which is needed from the start of the image capturing process until the subject 28 is released from the tomographic image capturing apparatus 10 can be reduced.

Furthermore, since a simple image capturing process does not generate a reconstructed tomographic image unlike a tomosynthesis image capturing process, the image capturing load posed by the simple image capturing process is smaller than the image capturing load posed by the tomosynthesis image capturing process. In addition, the period of time required to perform a simple image capturing process is shorter than the period of time required to perform a tomosynthesis image capturing process. Accordingly, when a simple image capturing process is performed, as part of a tomosynthesis image capturing process, prior to a tomosynthesis image capturing process, between the tomosynthesis image capturing processes, or while a reconstructed tomographic image is being generated, the period of time required to perform all the image capturing processes is shortened and hence the application of an unwanted radiation to the subject 28 is reduced even if the tomographic image capturing apparatus 10 is supplied with ordering information which includes both a tomosynthesis image capturing process and a simple image capturing process.

When a simple image capturing process is performed while a tomosynthesis image capturing process is being performed, the doctor 50 does not need to take the trouble of confirming a simple captured image, and no positioning of the subject 28 is necessary for each of the image capturing processes. In addition, the storage capacity for the generated image data can be reduced, and the processing load is also reduced. Specifically, a tomosynthesis image capturing process and a simple image capturing process are performed essentially in the same position, i.e., the positions P5, Q5, and radiographic images of subject 28 can efficiently be captured by performing a simple image capturing process as part of a tomosynthesis image capturing process.

If a plurality of successive tomosynthesis image capturing processes are performed, then since the image processor 42 generates a plurality of reconstructed tomographic images by way of parallel processing, the CPU of the control device 22 tends to undergo load concentration, and the processing rate is liable to drop sharply due to swapping caused by a memory shortage, resulting in difficulty generating the reconstructed tomographic images efficiently. According to the present embodiment, however, as a simple image capturing process is carried out between a plurality of tomosynthesis image capturing processes, it is possible to avoid the CPU load concentration and the sharp drop in the processing rate, making it possible to generate reconstructed tomographic images and simple captured images efficiently.

Moreover, when the radiation source 12 is moved to positions P1, P3, P5, P7 and P9 (skipping positions P2, P4, P6 and P8) in the forward stroke by the first moving mechanism 16, the radiation source 12 applies the radiation 20 to the subject 28 from the unskipped positions P1, P3, P5, P7, P9 (at angles θ), and the image capturing controller 40 determines whether the tomosynthesis image capturing process needs to be performed again or not, using the reconstructed tomographic image based on the image data at the positions P1, P3, P5, P7 and P9. Consequently, the image capturing controller 40 can determine whether the tomosynthesis image capturing process needs to be performed again or not in a shorter period of time than if it determines whether the tomosynthesis image capturing process needs to be performed again or not based on reconstructed tomographic images generated after the radiation source 12 has been moved in the forward and backward strokes or than if images are captured when the radiation source 12 is moved at smaller intervals in one direction.

When the image capturing sequence setting section 44 is supplied with new ordering information from the input unit 24, the image capturing sequence setting section 44 re-establishes an image capturing sequence for performing a simple image capturing process indicated by the new ordering information while a reconstructed tomographic image is being generated in the tomosynthesis image capturing process or between a plurality of tomosynthesis image capturing processes. Accordingly, the period of time required to capture images of the subject 28 can be shortened even if new additional ordering information is input while an image capturing process is being performed.

Although certain preferred embodiments of the present invention have been shown and described in detail, it should be understood that various changes and modifications may be made therein without departing from the scope of the appended claims.

What is claimed is:

1. A tomographic image capturing apparatus comprising:
    a radiation source for applying radiation to a subject at a plurality of different angles with respect to the subject;
    a radiation detector for detecting the radiation which has passed through the subject at each of the different angles and converting the detected radiation into image data;
    a tomographic image reconstructing unit for processing the image data into a reconstructed tomographic image; and
    an image capturing sequence setting unit for establishing an image capturing sequence of a tomosynthesis image capturing process and a simple image capturing process based on ordering information which represents the tomosynthesis image capturing process for acquiring the reconstructed tomographic image and the simple image capturing process for acquiring a simple captured image.

2. A tomographic image capturing apparatus according to claim 1, wherein the image capturing sequence setting unit establishes the image capturing sequence for performing the simple image capturing process separately from the tomosynthesis image capturing process based on the ordering information, and the radiation has a higher dose in the simple image capturing process than in the tomosynthesis image capturing process.

3. A tomographic image capturing apparatus according to claim 1, wherein the image capturing sequence setting unit establishes the image capturing sequence for performing the simple image capturing process within the tomosynthesis image capturing process based on the ordering information, and wherein the simple image capturing process is performed within the tomosynthesis image capturing process while the radiation source is applying the radiation at a higher dose when the radiation source is located substantially perpendicularly to a lying surface on which the subject lies, than when the radiation source is located at other different angles with respect to the subject.

4. A tomographic image capturing apparatus according to claim 1, further comprising:
    an image capturing base for supporting the subject lying thereon; and
    a moving mechanism for moving the radiation source in a forward stroke and a backward stroke along the subject;
    wherein the simple image capturing process is performed by applying the radiation from the radiation source to the subject when the radiation source is moved by the moving mechanism to such a position that the radiation source is located substantially perpendicularly to a lying surface of the image capturing base on which the subject lies.

5. A tomographic image capturing apparatus according to claim 4, wherein the moving mechanism moves the radiation source in the forward stroke and the backward stroke while skipping positions;
    the radiation source applies the radiation from unskipped positions at respective unskipped angles in the forward stroke and/or the backward stroke to the subject; and
    the tomographic image reconstructing unit processes the image data which are produced by moving the radiation source in the forward stroke and/or the backward stroke, into the reconstructed tomographic image.

6. A tomographic image capturing apparatus according to claim 1, wherein if the ordering information includes a plurality of tomosynthesis image capturing processes and a simple image capturing process, the image capturing sequence setting unit establishes the image capturing sequence for performing the simple image capturing process prior to each of the tomosynthesis image capturing processes or while the reconstructed tomographic image is being generated in each of the tomosynthesis image capturing processes.

7. A tomographic image capturing apparatus according to claim 1, further comprising an input unit for inputting the ordering information thereto;
    wherein the image capturing sequence setting unit establishes the image capturing sequence based on the ordering information when the ordering information is externally input to the input unit.

8. A tomographic image capturing apparatus according to claim 7, wherein when new ordering information is externally input to the input unit while an image of the subject is being captured, the image capturing sequence setting unit re-establishes the image capturing sequence for performing the simple image capturing process indicated by the new ordering information while the reconstructed tomographic image is being generated in the tomosynthesis image capturing process or between a plurality of tomosynthesis image capturing processes.

9. A tomographic image capturing method of applying radiation from a radiation source to a subject at a plurality of different angles with respect to the subject, detecting the radiation which has passed through the subject at each of the different angles and converting the detected radiation into image data, with a radiation detector, and processing the image data into a reconstructed tomographic image with a tomographic image reconstructing unit, comprising the step of:

establishing, with an image capturing sequence setting unit, an image capturing sequence of a tomosynthesis image capturing process and a simple image capturing process based on ordering information which represents the tomosynthesis image capturing process for acquiring the reconstructed tomographic image and the simple image capturing process for acquiring a simple captured image.

* * * * *